(12) United States Patent
Shalaby

(10) Patent No.: US 7,244,445 B2
(45) Date of Patent: Jul. 17, 2007

(54) CONFORMABLE, ABSORBABLE, SOLID COMPOSITE PREFORMS AND THEIR USE FOR BONE TISSUE ENGINEERING

(75) Inventor: Shalaby W. Shalaby, Anderson, SC (US)

(73) Assignee: Poly Med, Inc, Anderson, SC (US)

( * ) Notice: Subject to any disclaimer, the term of this patent is extended or adjusted under 35 U.S.C. 154(b) by 844 days.

(21) Appl. No.: 10/626,894

(22) Filed: Jul. 24, 2003

(65) Prior Publication Data

US 2004/0127995 A1 Jul. 1, 2004

Related U.S. Application Data

(60) Provisional application No. 60/399,203, filed on Jul. 29, 2002.

(51) Int. Cl.
*A61F 2/00* (2006.01)
*A61F 2/28* (2006.01)

(52) U.S. Cl. ................. 424/426; 623/23.56; 623/23.58

(58) Field of Classification Search ..................... None
See application file for complete search history.

(56) References Cited

U.S. PATENT DOCUMENTS

| | | | |
|---|---|---|---|
| 4,670,286 A * | 6/1987 | Nyilas et al. ............... 427/2.24 |
| 5,529,736 A * | 6/1996 | Shalaby et al. ............. 264/162 |
| 6,342,065 B1 * | 1/2002 | Shalaby ..................... 606/230 |
| 6,485,749 B1 * | 11/2002 | Shalaby ..................... 424/486 |
| 6,989,034 B2 * | 1/2006 | Hammer et al. .......... 623/23.72 |
| 7,048,753 B2 * | 5/2006 | Shalaby ..................... 606/230 |
| 7,192,437 B2 * | 3/2007 | Shalaby ..................... 606/230 |
| 2006/0093645 A1 * | 5/2006 | Janas et al. .................. 424/423 |
| 2007/0016302 A1 * | 1/2007 | Dickman .................. 623/17.13 |

OTHER PUBLICATIONS

Hollinger, Biomedical Applications of Synthetic Biodegradeable Polymer, 1995, Chapter 9, CRC Press, New York.
Zhang, Journal of Biomedical Research, 2002, 61, 1.
Yokoyama, Biomaterials, 2002, 23, 1091.
Zhao, Biomaterials, 2993, 23, 3227.
Kawamura, Journal of Biomedical Material Research, 2000, 50, 184.
Andriano, J. Biomedical Material Research-Applied Biomaterials, 2000, 53, 36.

* cited by examiner

*Primary Examiner*—Raymond J. Henley, III
(74) *Attorney, Agent, or Firm*—Leigh P Gregory

(57) ABSTRACT

The present invention is directed to an absorbable, conformable composite preform for use in making a solid bone filler which is an absorbable mixture of oppositely charged, solid microparticulate polyelectrolytes encased in a sealed, flexible, absorbable copolyester fabric construct and is capable of undergoing solidification to a solid, integral mass having a modulus of more than about 0.5 GPa upon contact with an aqueous medium. In an alternative embodiment the absorbable copolyester fabric construct is filled with a mixture of a microparticulate zincophosphate glass or glass-ceramic and at least one material carrying both acidic and basic groups on the same molecule.

19 Claims, No Drawings

CONFORMABLE, ABSORBABLE, SOLID COMPOSITE PREFORMS AND THEIR USE FOR BONE TISSUE ENGINEERING

RELATED APPLICATIONS

This application claims the benefit of U.S. Provisional Application 60/399,203 filed Jul. 29, 2002 and which is incorporated herein by reference.

BACKGROUND OF THE INVENTION

A major area in the clinical application of biomaterials that presents a formidable challenge to clinicians, material scientists, and bioengineers pertains to their use for the repair/replacement of bone tissues and particularly craniomaxillofacial bones. Related to this are (1) the inability of most biomaterials to form an active interface with natural tissues; (2) the limited availability of materials with tailored half life to allow the natural tissues to grow gradually and predictably into defective sites, temporarily occupied by a transient absorbable scaffold designed to support bone ingrowth; (3) scarcity of biomaterials that can be applied easily and precisely in irregular defective sites; (4) lack of bioactive biomaterial inserts or scaffolds for bone regeneration that conform to irregular structurally defective sites and transform into solid articles having a modulus that approaches those of typical bones; and (5) complications associated with occasional release of transition metallic ions from metallic implants that may cause allergic reactions in certain patients. Although great efforts were directed towards addressing these issues in orthopedic implants, limited attention was given to craniomaxillofacial implants. The promise of tissue engineering and particularly, directed tissue ingrowth about the implant, or what can be denoted, in situ tissue engineering, have created new, practical directions in dealing with current implants for bone repair or replacement. The latter are mostly metallic and designed for mechanical interlocking with bone or use in conjunction with bone cement.

In spite of the relatively limited attention given to the craniomaxillofacial implants by clinicians pertinent to concerns about the use of metallic materials, impressive efforts have been made by biomaterial scientists to explore the use of absorbable polymeric materials. This is understandable if one acknowledges the fact that in most craniomaxillofacial applications, the load-bearing requirements for the implants are generally much lower than those noted for orthopedic implants. And the less demanding mechanical requirements for craniomaxillofacial implants were very much in concert with the relatively low modulus of polymers as compared to metals. This, in turn, provided a strong incentive to explore the use of bioabsorbable polymers over the last three decades. However, limited availability of these polymers in terms of types and forms has compromised their acceptance by clinicians. Of the craniomaxillofacial family of implants, the maxillofacial subfamily, and more specifically, the intraoral implants, attracted the attention of most investigators. In their study of the intraoral implants, these investigators used absorbable polymers for repairing maxillary, mandibular, and facial bone defects. Commercial and experimental polymers used by these investigators were, for the most part, based on homopolymers such as poly(l-lactide) (PLLA), random copolymers of l-lactide/dl-lactide (PDLL), l-lactide/trimethylene carbonate (PLL/TMC), polyglycolide (PGA), terpolymers of l-lactide, d-lactide and glycolide (PDLLG), self-reinforced polyglycolide (SR-PGA), and to a lesser extent, poly p-dioxanone (PDS), as well as blends of these polymers. Unfortunately, in most of the explored applications, these materials did not meet fully the general requirements for successful craniomaxillofacial and particularly the intraoral, implants, namely: (1) mechanical and chemical stability during the expected period of functional performance; (2) biomechanical compatibility of the implant and surrounding bone, primarily in terms of modulus; (3) ability to support osseointegration and, hence, a timely healing and mechanical stability; and (4) ease of fabrication and shape modulation. Applications of bioabsorbable polymers as maxillofacial surgical implants have been reviewed by Mayer and Hollinger [Chapter 9 in *Biomedical Applications of Synthetic Biodegradable Polymer*, J. O. Hollinger, Ed., CRC Press, New York, 1995]. Most of these and more recent applications dealt with the use of (1) PLA sutures for internal fixation of iatrogenic mandibular symphysis fracture in monkeys; (2) PDLLA rods for the fixation of mandibular fractures in monkeys; (3) PLA plates and screws for reducing mandibular fractures in monkeys; (4) PDS lag screws for the fixation of a fracture of the mandibular angle; (5) PLA/PGA bone plates reinforced with PGA fabric for repairing mandibular and skull fractures; (6) PDS plates for orbital floor reconstruction; (7) SR-PLLA plates for the fixation of unfavorable transverse osteotomies; and (8) PLA plates and screws for the fixation of zygomatic arch fractures in rabbit. In practically all of the aforementioned craniomaxillofacial applications, the type of polymeric materials and the form of the implants were less than ideal because the limitation imposed on the clinical and scientific investigators in terms of availability of site-specific polymer types and forms. And this was the driving force to pursue the present invention.

Accordingly, this invention deals with an absorbable microparticulate mixture encased in a textile construct to form a sealed conformable article which transforms to a biocompatible, rigid mass that supports bone regeneration as part of in situ (or locally directed) tissue engineering. Although there have been a large number of citations in the prior art dealing with bone regeneration, none has dealt with the novel approach to bone regeneration described in this invention. Typical examples of the prior art are outlined below.

In an approach to the development of a novel scaffold for bone tissue engineering, Zhang and Zhang [*Journal of Biomedical Material Research*, 61, 1, (2002)] prepared a three-dimensional composite scaffold of macroporous HAP/β-TCP bioceramic matrices nesting chitosan. In comparison with pure porous bioceramics, the nested chitosan sponges enhanced the mechanical strength via reinforcement of the bioceramic matrix. The nested chitosan sponges also caused the composite scaffolds to have a high surface area/volume ratio leading to an increase in the number of cells adhered to the composite scaffolds. The results of the simulated body fluid experiments showed that a high density of randomly oriented, needlelike apatites have grown on the scaffold surface, suggesting that the material has good bioactivity. The cell culture experiments showed that MG63 osteoblast cells were attached and proliferated on the surface of the composite scaffold and migrated onto the pore walls. The cells have almost the same alkaline phosphatase activity on the composite scaffolds as on tissue culture dishes during the first 11 days of culture.

Towards the development of a new bone substitute material, Yokoyama and coworkers [*Biomaterials*, 23, 1091, (2002)] prepared a calcium phosphate cement that consists of chitosan, glucose, and citric acid solution as the liquid component, and tricalcium phosphate (α-TCP) and tetracalcium phosphate (TeCP) as the powder components. This cement could be molded to desired shape because of its chewing-gum-like consistency after mixing, and it demonstrated good biocompatibility in both soft and hard tissues. In this study, liquid components of 20% and 45% citric acid were used to investigate the influence of acid, and the results indicated that the concentration of citric acid in the liquid component influences both the mechanical properties and biocompatibility of the cement.

A communication by Zhao and coworkers [*Biomaterials*, 23, 3227, (2002)] described the preparation and histological evaluation of biomimetic, three-dimensional hydroxyapatite/chitosan-gelatin (HAP/CS-Gel) network as a composite scaffold for bone tissue engineering. In their study, the authors demonstrated the feasibility of using the phase separation technique to prepare such a scaffold. They further showed adhesion, proliferation, and expression of rat calvaria osteoblasts on these highly porous scaffolds. The HAP/CS-Gel composite scaffolds were characterized by their biomimetic composition, and further studies on cell densities, porosities of scaffolds as ell as in vivo implantation are underway.

Consistent findings on the role of zinc in bone growth prompted recent studies on the development and effectiveness of zinc-releasing calcium phosphate ceramics to promote bone formation with zinc-containing β-calcium phosphate (ZnTCP) ceramics as the zinc carrier [Kawamura, H. et al., *Journal of Biomedical Material Research*, 50, 184 (2000)]. A representative ceramic composite was made of ZnTCP and hydroxyapatite (HAP) having a Ca/P molar ratio of 1.60 at ZnTCP/HAP of 1.60. Thus, this composite was found to significantly promote mouse osteoblastic MC3T3-E1 cell proliferation in vitro at a zinc content of 1.2 weight percent. And bone formation about 1.60 ZnTCP/HAP implant in rabbit femur increased by 51% at zinc content of 0.316 weight percent in comparison with a composite of the same Ca/P molar ratio without zinc. Bone formation around monophasic ZnTCP implants in rabbit femora appeared to be a function of zinc content with a maximum bone formation at 00.316 weight percent. Interestingly, there was no statistically significant difference in the maximum bone formation due to ZnTCP and β-tricalcium phosphate at the same weight percent.

Bone morphogenic proteins (BMPs) have been shown to stimulate the production of bone in vivo when combined with an appropriate carrier material, such as collagen, calcium phosphate, or 2-hydroxyacid polymers [Ursit, M. R. in *Encyclopedia Handbook of Biomaterials & Bioengineering—Materials and Applications*, Vol. 1, Marcel Dekker, New York, 1995, pp. 1093-1122]. Recognizing the potential need for a puttylike absorbable matrix, which can be molded into shape of the desired new bone and hardened in situ by contact with aqueous fluids led Andriano and coworkers [*J. Biomedical Material Research—Applied Biomaterials*, 53, 36 (2000)] to develop a liquid polymer system consisting of lactide-glycolide copolymers dissolved in a "biocompatible" solvent which solidifies in situ by contact with aqueous fluid. The pursuit of this study was consistent with an earlier study by Chandrashekar and coworkers [*Proceedings of Portland Bone Symposium*, Portland, Oreg., August 1997, pp. 583-587] who incorporated BMPs in the same type of polymeric carrier system and used it to promote bone ingrowth in ectopic and orthotopic sites, such as subcutaneous and skull onlay, respectively. In their in vivo study of osteogenic potential BMPs delivered from the puttylike matrix, Andriano and coworkers first incorporated the proteins in a polymer matrix consisting of 50/50 poly(DL-lactide-co-glycolide) dissolved in N-methyl-2-pyrrolidone. The matrix was implanted in an 8 mm critical-size calvarial defect created in the skull of adult Sprague-Dawley rats (n=5 per treatment group). After 28 days, the implant sites were removed and examined for new bone formation, polymer degradation, and tissue reaction. Gamma-irradiated polymer matrices appeared to give more bone formation than non-irradiated samples (histological analysis: 2.76±1.34 mm$^2$ of bone versus 1.30±0.90 mm$^2$ of bone, respectively, and X-ray analysis: 27.2±15.9 mm$^2$ of bone versus 20.7±16.7 mm$^2$ of bone, respectively) and less residual polymer (0.0±0.0 versus 0.2±0.4, respectively). The polymer implants with bone morphogenic proteins also gave less inflammatory response than the polymer controls (gamma irradiated polymer/BMPs=1.8±0.4 and non-irradiated polymer/BMPs=1.2±0.4 versus polymer only=3.0±1.2, respectively).

SUMMARY OF THE INVENTION

The present invention is directed to an absorbable, conformable composite preform for use in making a solid bone filler which is an absorbable mixture of oppositely charged, solid microparticulate polyelectrolytes encased in a sealed, flexible, absorbable copolyester fabric construct and is capable of undergoing solidification to a solid, integral mass having a modulus of more than about 0.5 GPa upon contact with an aqueous medium.

The present invention is also directed to an absorbable, conformable composite preform for use in making a solid bone filler which is a mixture of a microparticulate zincophosphate glass or glass-ceramic and at least one material carrying both acidic and basic groups on the same molecule, wherein the mixture is encased in a sealed flexible, absorbable copolyester fabric construct, and wherein the preform is capable of undergoing solidification to a solid, integral mass having a modulus of more than about 0.5 GPa upon contact with an aqueous medium.

DETAILED DESCRIPTION OF PREFERRED EMBODIMENTS

This invention deals, in general, with an absorbable, highly conformable composite preform comprising a mixture of oppositely charged organic and inorganic solid microparticulate polyelectrolytes encased in a flexible fabric construct, wherein such a combination yields a highly conformable article that can be fit, precisely, into an irregular bone defect and solidifies or cures into a cytocompatible, rigid mass, which can support bone regeneration and gradually absorbs and it is replaced by bone tissue through the pathway of in situ or locally directed tissue engineering. More specifically, the construct, subject of this invention, can be used as a preform for in situ tissue engineering of craniomaxillofacial bones. In another aspect of this invention, the absorbable composite preform is used for in situ tissue engineering of long bones and in repairing herniated intervertebral discs.

One specific aspect of this invention deals with absorbable preforms comprising (1) microparticulates of a fast-absorbing (or dissolving) polymeric phosphate glass or ceramic based on dibasic ammonium dihydrogen phosphate, calcium dioxide, and sodium carbonate, present as an anionic polyelectrolyte; and (2) microparticulate chitosan (80-90% deacetylated chitin) as a cationic polyelectrolyte. The microparticulate polyelectrolytes are encased in a knitted, heat-sealed fabric. The knitted fabric may be coated with an absorbable thin coating to reduce its porosity. The knitted fabric may also be reacted under free radical conditions with maleic anhydride, followed by hydrolysis, to introduce carboxylic functionality to the surface of the fabric. The carboxylated surface can be used to ionically immobilize tissue growth promoters such as BMPs or a recombinant basic fibroblast-derived growth factor (FGF-1) to eventually promote the bone regeneration about the preform after its solidification within the implant site. An alternate method to provide carboxylic groups on the surface is to use carboxyl-bearing copolyester for coating the knitted fabric and allowing the FGF-2 to bind ionically to the anionic coating.

In another aspect of this invention, the fabric enclosure is constructed from multifilament yarn made from segmented high lactide copolymer. Another aspect of this invention deals with the microparticulate mixture of the preform being a moderately absorbable zinco-phosphate glass and chitosan. Another aspect of this invention deals with the microparticulate mixture of the preform made of a slow-absorbing silico-phosphate glass and chitosan. Other compositions of the microparticulate blend of the enclosure are depicted in Table I. Several examples of the typical preform components are illustrated in Table II.

TABLE I

Composition of the Preforms, Powder Components, and Their Blends for In Vitro Screening

| Component | | | Blend | | | | | | | | | | | | | | | |
|---|---|---|---|---|---|---|---|---|---|---|---|---|---|---|---|---|---|---|
| Main Type | Composition | No. | B1 | B2 | B3 | B4 | B5 | B6 | B7 | B8 | B9 | B10 | B11 | B12 | B13 | B14 | B15 | B16 |
| Fast-absorbing phosphate glass | Polyphosphate containing Na, Ca, & Mg | FP-1 | X | — | — | — | — | — | — | — | — | — | — | — | — | — | — | — |
| | | FP-2 | — | X | X | — | — | — | — | — | — | — | — | — | — | — | — | — |
| Moderately absorbing zinco-phosphate glasses | Polyphosphate containing Na, Ca, & Zn | MP-1 | — | — | — | X | — | — | — | — | — | X | X | X | — | — | — | — |
| | | MP-2 | — | — | — | — | X | X | — | — | — | — | — | — | X | X | — | — |
| Slow-absorbing silico-phosphate glasses | Polyphosphate containing CA, Zn, Na, & Si | SP-1 | — | — | — | — | — | — | X | — | — | — | — | — | — | — | X | X |
| | | SP-2 | — | — | — | — | — | — | — | X | X | — | — | — | — | — | — | — |
| Fast-absorbing Anionic polyester | Acid-terminated Polyglycolide | PG-A1 | — | — | — | — | — | — | — | — | — | X | — | — | X | X | — | — |
| | | PG-A2 | — | — | — | — | — | — | — | X | — | — | X | — | — | — | X | X |
| Slow-absorbing Copolyester | Acid-terminated PLG | PLG-A | — | — | — | — | — | — | — | — | — | — | — | X | — | — | — | — |
| Cationic polyester | Amine-bearing PGA | PG-N | — | — | — | — | — | — | — | — | — | X | X | — | X | X | — | — |
| | Amine-bearing PLG | PLG-N | — | — | — | — | — | — | — | — | — | — | — | X | — | — | X | X |
| Chitosan | 90% deacetylated Chitosan | CS | X | X | — | X | X | X | X | X | X | X | X | X | X | X | X | X |
| Less-hydrophilic Chitosan | Partially propionylated CS | CS-P | — | — | X | — | — | — | — | — | — | — | — | — | X | — | — | — |
| Anionic Chitosan | Glutarylated CS | CS-G | — | — | — | — | — | — | X | — | — | X | — | — | — | X | — | — |
| | Propionylated/ Glutarylated CS | CS-PG | — | — | — | — | — | X | — | — | — | — | — | — | — | — | X | X |
| Cationic polysaccharide | Chondroitin Sulfate-A | CSA | — | — | — | — | — | — | — | — | X | — | X | — | X | — | — | — |
| Polylysine (PLS) | Low DP PLS | PLS | — | — | X | — | — | — | X | X | — | — | — | — | X | X | X | — |
| Excipient | Glucose | GL | — | — | — | — | X | — | — | X | — | — | — | X | — | — | — | — |

TABLE II

Compositions of Assembled Candidate Preform

| Components | PF 1 | PF 2 | PF 3 | PF 4 | PF 5 | PF 6 | PF 7 | PF 8 | PF 9 | PF 10 | PF 11 | PF 12 | PF 13 | PF 14 | PF 15 | PF 16 | PF 17 | PF 18 | PF 19 | PF 20 | PF 21 |
|---|---|---|---|---|---|---|---|---|---|---|---|---|---|---|---|---|---|---|---|---|---|
| Powder[1]: | | | | | | | | | | | | | | | | | | | | | |
| B1 | X | — | — | — | — | — | — | — | — | — | — | — | — | — | — | — | — | — | — | — | — |
| B2 | — | X | — | — | — | — | — | — | — | — | — | — | — | — | — | — | — | — | — | — | — |
| B3 | — | — | X | — | — | — | — | — | — | — | — | — | — | — | — | — | — | — | — | — | — |
| B4 | — | — | — | X | — | — | — | — | — | — | — | — | — | — | — | — | — | — | — | — | — |
| B5 | — | — | — | — | X | — | — | — | — | — | — | — | — | — | — | — | — | — | — | — | — |
| B6 | — | — | — | — | — | X | — | — | — | — | — | — | — | — | — | — | — | — | — | — | — |
| B7 | — | — | — | — | — | — | X | — | — | — | — | — | — | — | — | — | — | — | — | — | — |
| B8 | — | — | — | — | — | — | — | X | — | — | — | — | — | — | — | — | — | — | — | — | — |
| B9 | — | — | — | — | — | — | — | — | X | — | — | X | — | — | — | — | — | — | — | — | — |
| B10 | — | — | — | — | — | — | — | — | — | X | — | — | — | — | — | — | — | — | — | — | — |
| B11 | — | — | — | — | — | — | — | — | — | — | X | — | — | — | — | — | — | — | — | — | — |
| B12 | — | — | — | — | — | — | — | — | — | — | — | X | — | X | — | X | — | — | — | — | — |
| B13 | — | — | — | — | — | — | — | — | — | — | — | — | X | — | X | — | — | — | — | — | — |
| B14 | — | — | — | — | — | — | — | — | — | — | — | — | — | — | — | — | X | — | — | — | — |
| B15 | — | — | — | — | — | — | — | — | — | — | — | — | — | — | — | — | — | X | X | — | — |
| B16 | — | — | — | — | — | — | — | — | — | — | — | — | — | — | — | — | — | — | — | — | X |

TABLE II-continued

Compositions of Assembled Candidate Preform

| Components | PF 1 | PF 2 | PF 3 | PF 4 | PF 5 | PF 6 | PF 7 | PF 8 | PF 9 | PF 10 | PF 11 | PF 12 | PF 13 | PF 14 | PF 15 | PF 16 | PF 17 | PF 18 | PF 19 | PF 20 | PF 21 |
|---|---|---|---|---|---|---|---|---|---|---|---|---|---|---|---|---|---|---|---|---|---|
| Fabric[2]: | | | | | | | | | | | | | | | | | | | | | |
| KF1 | — | — | — | — | X | — | — | — | — | — | X | X | X | — | — | — | X | — | — | — | — |
| KF2 | X | — | — | — | — | X | X | X | — | — | — | — | — | — | — | — | — | — | — | — | — |
| KF1-A | — | — | X | X | — | — | X | — | — | X | — | — | — | X | X | X | — | X | X | X | X |
| KF1-N | — | — | — | — | — | — | — | — | X | — | — | — | — | — | — | — | — | — | — | — | — |
| Coating[3]: | | | | | | | | | | | | | | | | | | | | | |
| PCLG-1 | — | — | — | — | — | — | X | — | — | — | — | X | — | — | — | — | — | X | X | X | X |
| PCLG-2 | — | — | — | — | X | X | — | X | X | — | — | — | X | — | — | — | — | — | — | — | — |
| SLC3 | X | X | X | X | — | — | — | — | — | X | — | — | — | — | — | X | — | — | — | — | — |
| FGF-2[4] | X | X | X | X | X | X | — | X | — | X | X | — | X | X | X | X | X | X | X | X | X |

[1]Powder blends of oppositely charged organic and inorganic polyelectrolytes, with and without glucose as porogen.
[2]KF1 and KF2 knitted fabric with low- and high-degree of porosity, respectively; KF1-A and KF1-N knitted fabric with acidic and basic surfaces, respectively.
[3]PCLGs = low molecular weight. Caprolactone/glycolide copolymer with one or two carboxylic groups/chain; SLC3 = high molecular weight segmented lactide copolymer.
[4]FGF-2 = basic fibroblast-derived growth factor.

Another aspect of this invention deals with a solid microparticulate mixture of the preform comprising an absorbable zincophosphate glass and one or more polypeptide carrying basic or acid side groups such as polylysine or polyaspartic acid and polyglutamic acid, respectively.

Another aspect of this invention deals with a solid microparticulate mixture of the preform comprising an absorbable zincophosphate glass and one or more organic material carrying both basic and acidic groups in the same molecule such as the amino acids glycine, lysine, glutamic acid, and aspartic acid. Another aspect of the invention deals with a solid microparticulate mixture of the preform comprising a polymeric phosphate that may be a zincophosphate glass, one or more material carrying basic as well as acidic groups such as glycine or glutamic acid, and/or a divalent metal salt having an affinity for water such as anhydrous calcium sulfate and calcium phosphate.

Another aspect of the invention deals with use of the composite preform as a cranial cover. Another aspect of the invention deals with the use of the composite preform for replacing accidentally or pathologically lost bone in an orbital cavity. Another aspect of this invention deals with use of the composite preform for replacing accidentally or pathologically lost facial bone. Another aspect of this invention deals with composite preforms for correcting skeletal bones as part of plastic surgery or disfigured bone tissues.

Additional illustrations of this invention are provided in the following examples.

EXAMPLE 1

Preparation of Fast-absorbing, Low Molecular Weight Acid-terminated Polyglycolides These are prepared using glycolide with glycolic or malic acid as the initiator to form PG-A1 and PG-A2, respectively. Stannous octoate is used as the ring-opening polymerization catalyst using similar schemes to those described by Shalaby [Shalaby, S. W., U.S. Pat. No. 5,607,686 (1997)]. The polymers are characterized for composition and identity (IR, NMR) thermal properties (DSC), carboxyl content (acidimetry), and molecular weight (GPC).

EXAMPLE 2

Preparation of Slow-absorbing, Low Molecular Weight Acid-terminated Poly(l-lactide-co-glycolide)

A mixture of l-lactide and glycolide is prepared as described in Example 1 using glycolic acid as the initiator for the formation of a copolymer (PLG-A) having less than 95 percent of lactide-based sequences.

EXAMPLE 3

Preparation of Fast-absorbing, Low Molecular Weight Nitrogenous Polyglycolide (PG-N)

Glycolide is polymerized as in Example 1 with the exception of using triethanolamine instead of citric acid as the initiator. The amine content of the polymer is determined by acidimetry and elemental analysis.

EXAMPLE 4

Preparation of Slow-absorbing, Low Molecular Weight Nitrogenous 90/10 l-Lactide/Glycolide Copolymer (PLG-N)

The polymer is prepared and characterized as described in Example 2 with the exception of using triethanolamine instead of glycolic acid at 30% of the noted stoichiometry. The amine content is determined as noted in Example 3.

EXAMPLE 5

Preparation of High Molecular Weight Fiber-forming Essentially Random l-Lactide/Glycolide Copolymers (PLG-1 and PLG-2)

The preparation of 95/5 and 5/95 l-lactide/glycolide copolymers, namely PLG-1 and PLG-2, respectively, is achieved by ring-opening polymerization using the required amount of cyclic monomers in the presence of 1-decanol as an initiator and stannous octoate as a catalyst as described earlier [Benicewicz, B. C. et al., Chapter 14 in *Agriculture* and *Synthetic Polymers* (J. E. Glass and G. Swift, Eds.), American Chemical Society, Washington, D.C., 1990; Shalaby, S. W. and Johnson, R. A. in *Biomedical Polymers: Designed to Degrade Systems* (S. W. Shalaby, Ed.), Hanser Publishing Company, New York, 1994]. The polymers are characterized for identity (IR, NMR), molecular weight (in terms of inherent viscosity, I.V.), and thermal properties (DSC).

EXAMPLE 6

Preparation of Segmented 88/12 l-Lactide/Trimethylene Carbonate Copolymer (SLC-1)

The polymer is prepared using a prepolymer of trimethylene carbonate (TMC) that is end grafted with l-lactide and TMC as described by Shalaby [Shalaby, S. W., U.S. Pat. No. 6,395,259 (2002)]. The copolymer is characterized for identity (NMR, IR), molecular weight (IV and GPC), and thermal properties (DSC).

EXAMPLE 7

Preparation of Segmented 75/10/20 l-Lactide/Glycolide/TMC Copolymer (SLC-2)

This is prepared and characterized as described for SLC-1 with the exception of using a mixture of glycolide (G) and TMC for the preparation of the prepolymer and a mixture of l-lactide/glycolide for final end-grafting.

EXAMPLE 8

Preparation of Film-forming Compliant L/CL/TMC Terpolymers (SLC-3)

This is prepared and characterized as described for SLC-2 with the exception of using the polyaxial prepolymer and less than 70% l-lactide (Shalaby, S. W. et al., U.S. Patent Application (Polyaxial Prepolymers and Crystalline Copolyesters Therefrom), filed 2000].

EXAMPLE 9

Preparation of Low Molecular Weight Basic 95/5 Caprolactone/Glycolide Copolymeric Coating (PCLG-1)

This is prepared using a 95/5 mixture of ε-caprolactone and glycolide in the presence of triethanolamine as an initiator and stannous octoate as the catalyst under conditions similar to those used earlier by Shalaby [Shalaby, S. W., U.S. Pat. No. 5,522,842 (1996)]. The amount of initiator is adjusted to limit the polymer molecular weight ($M_n$) to about 5 kDa. The polymer will be characterized for identity (NMR, IR) and molecular weight (GPC).

EXAMPLE 10

Preparation of Low Molecular Weight Carboxy-bearing 95/5 Caprolactone/Glycolide Copolymeric Coating (PCLG-2)

This is prepared and characterized as noted for its basic counterpart in Example 8, with the exception of using malic acid as the initiator in such an amount so as to produce a copolymer having an $M_n$ of about 5 kDa.

EXAMPLE 11

Acylation of Chitosan with Propionic Anhydride

Microparticulates of high purity, commercial chitosan (CS), with 80-90 deacetylated chitin repeat units, is partially acylated with propionic anhydride to form CS-P to reduce the free amine-bearing sequences to about 60% and create a paraffin-rich hydrophobic surface. The acylation and product characterization is conducted using similar schemes to those used earlier (Shalaby, S. W. et al., U.S. Pat. No. 5,665,702 (1997); Shalaby, S. W. et al., U.S. Pat. No. 5,821,221 (1998)].

EXAMPLE 12

Acylation of Chitosan with Glutaric Anhydride

Using a similar acylation scheme to that reported by Shalaby and coworkers (Shalaby, S. W. et al., U.S. Pat. No. 5,665,702 (1997); Shalaby, S. W. et al., U.S. Pat. No. 5,821,221 (1998)], practically all free amine groups of chitosan will be acylated with glutaric anhydride to form CS-G. The product is isolated and characterized as described earlier (Shalaby, S. W. et al., U.S. Pat. No. 5,665,702 (1997); Shalaby, S. W. et al., U.S. Pat. No. 5,821,221 (1998)]. The acid content is determined using acidimetry.

EXAMPLE 13

Mixed Acylation of Chitosan

This entails acylating about 50 percent of the free amine groups of CS with propionic anhydride as in Example 11, followed by acylating practically all the remaining amine groups with glutaric anhydride as in Example 12. This yields a relatively hydrophobic anionic chitosan (CS-PS).

EXAMPLE 14

General Method of Preparation

A mixture of ammonium dihydrogen ($NH_4H_2PO_4$) phosphate and two or more of the following oxides or salts are used depending on the desired final composition: sodium carbonate ($Na_2CO_3$), calcium oxide (CaO), magnesium oxide (MgO), zinc oxide (ZnO), and silicon dioxide ($SiO_2$). The mixtures are heated to the desired temperature (700-1200° C.) to yield vitrifiable liquids as described earlier [Shalaby et al., U.S. Pat. No. 5,874,509 (1999)]. The "molten glass" is poured rapidly onto cooled stainless steel sheets. After cooling to room temperature, the glass is isolated and ground to a size suitable for subsequent jet-milling. The jet-milled, microparticulate glass is tested for (1) composition (elemental analysis); (2) thermal properties (DSC); (3) solubility in water; and (4) particle size distribution (Accusizer and SEM). Solubility testing is then conducted on the ground and jet-milled particles to determine the effect of surface area on solubility.

EXAMPLE 15

Preparation of Fast-absorbing Polymeric Phosphate Glasses (FP)

These are prepared using $(NH_4)H_2PO_4$, CaO, MgO, and $Na_2CO_3$ at different ratios to produce two fast-absorbing glasses having absorption profiles that decrease from FP1 to FP2.

EXAMPLE 16

Preparation of Moderately Absorbing Polymeric Zinco-phosphate Glasses (MP)

Two of these glasses are prepared using $(NH_4)H_2PO_4$, CaO, ZnO, and $Na_2CO_3$ at different ratios to produce moderately absorbing glasses having absorption profiles that decrease from MP1 to MP2.

EXAMPLE 17

Preparation of Slow-absorbing Polymeric Silico-phosphate Glasses (SP)

Two of these glasses are prepared using $(NH_4)H_2PO_4$, CaO, ZnO, $Na_2CO_3$, and $SiO_2$ at different ratios to produce slow-absorbing glasses having absorption profiles that decrease from SP1 to SP2.

EXAMPLE 18

Processing and Characterization of Preform Components

This section covers (1) the process for particle size reduction of solid powders; (2) fiber spinning and conversion of yarn to knitted fabrics; and (3) surface modification of fabrics.

EXAMPLE 19

Size Reduction of Solid Powders

Synthetic powders of PG-1 and similar crystalline organic polymers or polymeric phosphate glasses with an average diameter of 100-150µ are jet-milled under a dry nitrogen atmosphere to produce the desired microparticle dimensions. The particle size analysis is determined using a particle size analyzer (Accusizer and SEM). Surface chemistry is determined using ESCA.

Microparticulate chitosan and derivatives are produced by nebulizing (using an ultrasonic atomizer) a suitable solution into a cooled non-solvent. The particles are isolated by centrifugation. The dry particles are characterized for particle size distribution and surface functionalities (ESCA).

EXAMPLE 20

Fiber Spinning and Conversion to Knitted Fabric

Fiber-forming polymers are melt spun into multifilament yarn. The yarn is knitted into two different types of woven fabrics, KF1 and KF2. The degree of porosity increases from KF1 to KF2.

EXAMPLE 21

Surface Modification of Fabrics

The surface of selected fabrics (KF1 of copolymer SLC-1) is modified to (1) introduce basic functionality through reaction of the surface with a solution of hydrazine (KF 1-N); (2) introduce acidic functionality through free-radical carboxylation of the surface (KF1-A); and (3) decrease the fabric porosity through spray- or dip-coating with an elastomeric copolymer (SLC-3), which may contain basic or acidic low molecular weight caprolactone/glycolide copolymer, PCLG-1 or PCLG-2, respectively.

EXAMPLE 22

Preparing Knitted Fabrics

Multifilament yarns of pre-determined denier and denier per filament are knitted using a circular knitting machine to produce knitted tubes. The knitting process is adjusted to produce circular knits with fabrics with two levels of porosity (low and high as KF1 and KF-2).

EXAMPLE 23

Coating Knitted Fabrics

Selected fabrics of copolymer SLC-1 are coated with basic (anionogenic) and acidic (cationogenic) coatings PCLG-1 and PCLG-2, respectively. The coating application is achieved by dipping or spraying (using an ultrasonic atomizer) the knitted tube in an acetone solution followed by drying. One coating level is used for both types of fabrics to provide practically sealed pores.

EXAMPLE 24

Assembling the Preforms

A mixture of the desired microparticles are transferred to partially heat-sealed knitted tubes (both coated and uncoated) to fill over 80 percent of the available volume. The filled tubes are heat-sealed further to provide the final preform. Compositions of the different preforms are provided in Table II. The basic coating may be premixed with FGF-2 and the acidic coating is ionically bound to FGF-2.

EXAMPLE 25

Curing (Solidification) of Assembled Preforms and Determining the Mechanical Properties of the Cured Devices Representative specimens of the assembled preforms are incubated in a buffered phosphate solution at 37° C. and pH 7.4 for 3, 6, 9, and 12 hours to determine an optimum time period for curing into rigid forms. Using such time period for curing, the candidate preforms are cured and their mechanical properties are determined in terms of strength and modulus in the compression and bending modes. Based on these results, most-promising candidates are selected for subsequent, more comprehensive evaluations.

EXAMPLE 26

Sterilization of Selected Preforms

Based on results of Example 25, most-promising types of preforms are sterilized in sealed packages under a nitrogen atmosphere using the radiochemical sterilization protocol described earlier [Correa, D. E. et al., *Sixth World Biomaterials Congress, Transactions of The Society of Biomaterials*, II, 992 (2000); Shalaby, S. W. and Linden, Jr., C. L., U.S. Pat. No. 5,422,068 (1995)].

EXAMPLE 27

In Vitro Mechanical Properties Retention of Mass Loss Cured Preforms

Representative preforms are cured under the optimum conditions identified in Example 25. The cured preforms are incubated in a phosphate buffer at 37° C. and pH 7.4 for 2, 4, 6, and 12 weeks. At the conclusion of these periods, the breaking strength and modulus in the compression and bending modes are determined. Mass loss at 3 and 6 months of cured preforms are determined under similar conditions.

EXAMPLE 28

Curing of a Microparticulate Mixture Preform Made of Phosphate Glass and Glycine A 10% solution of glycine in water was added to slow absorbing phosphate glass (made of 40 mole % $P_2O_5$, 30 ZnO, 30 CaO) in a 1 mL: 1 g ratio. The resulting paste was shown to harden into a hard, solid mass after curing at 37° C. for 1 hour.

EXAMPLE 29

Curing of a Microparticulate Mixture Preform Made of Differing Ratios of a Phosphate Glass to Glycine Based on the results of Example 28, different ratios of phosphate glass to glycine were prepared (2:1 and 1:1). Water was then added until the preform became pasty. Curing at 37° C. resulted in the formation of a hard, solid mass after 1 hour.

EXAMPLE 30

Curing of a Microparticulate Mixture Preform Made of Phosphate Glass, Glycine, and Calcium Sulfate ($CaSO_4$)

A mixture of equal amounts of phosphate glass (as in Example 28), glycine, and $CaSO_4$ was prepared and water was then added until the entire mixture became pasty. A hard, solid mass resulted after curing at 37° C. for 1 hour.

Preferred embodiments of the invention have been described using specific terms and devices. The words and terms used are for illustrative purposes only. The words and terms are words and terms of description, rather than of limitation. It is to be understood that changes and variations may be made by those of ordinary skill art without departing from the spirit or scope of the invention, which is set forth in the following claims. In addition it should be understood that aspects of the various embodiments may be interchanged in whole or in part. Therefore, the spirit and scope of the appended claims should not be limited to descriptions and examples herein.

What is claimed is:

1. An absorbable, conformable composite preform for use in making a solid bone filler comprising an absorbable mixture of oppositely charged, solid microparticulate polyelectrolytes encased in a sealed, flexible, absorbable copolyester fabric construct and capable of undergoing solidification to a solid, integral mass having a modulus of more than about 0.5 GPa upon contact with an aqueous medium.

2. An absorbable, conformable composite preform as set forth in claim 1 wherein one of the microparticulate polyelectrolytes comprises a positively charged chitosan.

3. An absorbable, conformable composite preform as set forth in claim 1 wherein one of the polyelectrolytes comprises a negatively charged polymeric phosphate glass or ceramic.

4. An absorbable, conformable composite preform as set forth in claim 1 wherein the oppositely charged polyelectrolytes comprise an ionic conjugate of a polymeric phosphate glass or ceramic and a chitosan.

5. An absorbable, conformable composite preform as set forth in claim 1 wherein at least one of the polyelectrolytes comprises a polypeptide having side groups selected from amino side groups and carboxylic side groups.

6. An absorbable, conformable composite preform as set forth in claim 5 wherein the polypeptide comprises polylysine.

7. An absorbable, conformable composite preform as set forth in claim 5 wherein the polypeptide is selected from polyaspartic acid and polyglutamic acid.

8. An absorbable, conformable composite preform as set forth in claim 1 wherein the flexible copolyester fabric construct comprises a high lactide segmented copolymer.

9. An absorbable, conformable composite preform as set forth in claim 1 wherein the surface of the flexible fabric construct comprises carboxylic groups and wherein at least one growth factor is ionically immobilized on the carboxylic groups.

10. An absorbable, conformable composite preform as set forth in claim 9 wherein the at least one growth factor comprises a basic fibroblast-derived growth factor (FGF-2).

11. An absorbable, conformable composite preform as set forth in claim 1 as a replacement for a lost part of a craniomaxillofacial bone.

12. An absorbable, conformable composite preform for use in making a solid bone filler comprising a mixture of a microparticulate zincophosphate glass or glass-ceramic and at least one material carrying both acidic and basic groups on the same molecule, wherein the mixture is encased in a sealed flexible, absorbable copolyester fabric construct, and wherein the preform is capable of undergoing solidification to a solid, integral mass having a modulus of more than about 0.5 GPa upon contact with an aqueous medium.

13. An absorbable, conformable composite preform as set forth in claim 12 wherein the at least one material carrying both acidic and basic groups comprises an amino acid selected from the group consisting of glycine, lysine, glutamic acid, and aspartic acid.

14. An absorbable, conformable composite preform as set forth in claim 13 further comprising calcium sulfate microparticulates.

15. An absorbable, conformable composite preform as set forth in claim 13 further comprising calcium phosphate microparticulates.

16. An absorbable, conformable composite preform as set forth in claim 12 wherein the flexible copolyester fabric construct comprises a high lactide segmented copolymer.

17. An absorbable, conformable composite preform as set forth in claim 12 wherein the surface of the flexible fabric construct comprises carboxylic groups and wherein at least one growth factor is ionically immobilized on the carboxylic groups.

18. An absorbable, conformable composite preform as set forth in claim 17 wherein the at least one growth factor comprises a basic fibroblast-derived growth factor (FGF-2).

19. An absorbable, conformable composite preform as set forth in claim 12 as a replacement for a lost part of a craniomaxillofacial bone.

* * * * *